United States Patent [19]

Gindler

[11] Patent Number: 4,497,792
[45] Date of Patent: Feb. 5, 1985

[54] SPECIMEN EMBEDDING COMPOSITION

[75] Inventor: E. Melvin Gindler, Union City, Calif.

[73] Assignee: Sherwood Medical Company, St. Louis, Mo.

[21] Appl. No.: 332,038

[22] Filed: Dec. 18, 1981

[51] Int. Cl.³ .............................................. G01N 33/48
[52] U.S. Cl. .......................................... 424/3; 427/2; 427/4; 524/487; 524/488; 524/489
[58] Field of Search ...................... 524/487, 488, 489; 427/2, 4; 424/3

[56] References Cited

U.S. PATENT DOCUMENTS

| | | | |
|---|---|---|---|
| 2,108,809 | 2/1938 | Fenzel | 106/270 |
| 2,371,473 | 3/1945 | Sanford | 106/270 |
| 2,776,596 | 1/1957 | Eigen | 88/40 |
| 2,877,196 | 3/1959 | Reding | 524/488 |
| 2,996,762 | 9/1969 | McCormick | 18/26 |
| 3,146,214 | 8/1964 | Jakaitis | 524/487 |
| 3,189,573 | 6/1965 | Oken | 524/87 |
| 3,386,936 | 6/1968 | Gordy | 524/489 |
| 3,466,209 | 9/1969 | Leveskis | 156/57 |
| 3,485,784 | 12/1969 | Waples | 524/87 |
| 3,527,863 | 9/1970 | Weichselbaum | 424/3 |
| 3,638,709 | 2/1972 | Brown, Jr. et al. | 156/57 |

FOREIGN PATENT DOCUMENTS

| | | | |
|---|---|---|---|
| 725715 | 1/1966 | Canada | 524/87 |
| 911527 | 11/1962 | United Kingdom | 524/87 |

OTHER PUBLICATIONS

"Preparing a Slice of Life" C. F. A. Culling, Lacer, Division of Sherwood Medical, St. Louis, Mo.
"Journal of Histotechnology", pp. 36 and 37, Mar. 1981.
"Resin Paraffin Additive" M. S. Judge, and p. 12, Lancer.
"Elvax" DuPont Company, Wilmington, Del. 11/80.
"Elvax, A Grade Selection Guide", DuPont 7/80.
Lancer-Product Information, "Paraplast and Paraplast Plus", Sherwood Medical, St. Louis, Mo.

Primary Examiner—Sam Silverberg
Attorney, Agent, or Firm—Stanley N. Garber; Gregory E. Upchurch; William R. O'Meara

[57] ABSTRACT

A histological specimen infiltrating and embedding composition including paraffin and a copolymer of ethylene and vinyl acetate. The copolymer may be between 0.5 and 5% by weight of the paraffin. A surface active compatibilizer soluble in molten paraffin and which reduces the turbidity of the molten paraffin may be added to the composition in an amount between about 0.4% and 2% by weight of the paraffin.

5 Claims, No Drawings

SPECIMEN EMBEDDING COMPOSITION

DESCRIPTION

TECHNICAL FIELD

This invention relates to paraffin-based embedding compositions used in the preparation of histological tissue specimens, and more particularly, to an improved composition for embedding tissue specimens for sectioning in a microtome for producing specimen sections for histological studies.

BACKGROUND ART

Paraffin had been used many years as an embedding medium in the preparation of tissue specimens for sectioning in a microtome to produce specimen sections for histological studies. Such embedding processes generally include the well known steps of specimen fixation, dehydration, clearing, paraffin infiltration or impregnation, blocking or embedding in a block of paraffin, slicing the block and specimen into thin sections, mounting the sections on slides, removing the paraffin and solvents employed for this purpose, and staining the sections. These are then readly for microscopic analysis. The primary purpose of the embedding medium is to permit the specimens to be sectioned and mounted in the natural state.

Some of the problems of using plain or ordinary paraffin wax, as purchased from the manufacturers of paraffin, as a specimen embedding material, have been that a relatively long period of time is required to adequately infiltrate the specimen and the inability to obtain a section as thin as desired and one that is flat and wrinkle-free. Paraffin tends to collapse and crumble, and especially when a relatively hard or brittle object is struck during sectioning. The compressibility of plain paraffin generally increases the chance of deforming the specimen section, and the thermal and mechanical shock properties are not as good as generally desired.

In attempts to improve paraffin as an histological embedding material and overcome some of the above mentioned problems, additives, such as various resins, beeswax and polymers, have been added. However, paraffin waxes differ greatly in thermal and mechanical characteristics since they are derived from crude oil taken from the earth at different locations throughout the world. Paraffin varies especially in content of linear and cyclic hydrocarbons which causes the large variations in mechanical and thermal properties among paraffin waxes suppled by different companies. Because of the differences in the paraffins, additives have resulted in improved paraffin embedding compositions but only when added to certain available paraffins. A serious problem has been the poor market availability of paraffin waxes which are suitable for use in the manufacture of emedding media. For example, some paraffin waxes are reltively soft and generally cannot be sliced sufficiently thin without tending to crack and crumble even when such additives were used.

In general, good paraffin based embedding materials now being marketed are capable of producing good specimen slices having thicknesses between about 2 and 5 microns. Where slices having a thickness of 1 micron are required, methacrylate and acrylate ester embedding materials have sometimes been used. However, the necessary polymerization reaction and the need of a special microtome having a glass knife blade to avoid dulling are prolems associated with the use of the latter materials. Paraffin based embedding media generally has not been entirely satisfactory for sections less than 2 microns in thickness and is relatively poor for 1 micron sections.

DISCLOSURE OF THE INVENTION

It is therefore an object of the present invention to provide an improved paraffin-based embedding material for embedding tissue specimens for clinical analysis which substantially overcomes one or more of the above mentioned problems.

In accordance with one aspect of the present invention, tissue specimen embedding material is provided which includes a mixture of paraffin and an effective amount of ethylene-vinyl acetate copolymer. In accordance with another aspect, an embedding material includes a mixture of paraffin, ethylene-vinyl acetate copolymer, and a compatibilizer.

These, as well as other objects and advantages of the present, will become more apparent from the following detailed description.

DETAILED DESCRIPTION OF A PREFERRED EMBODIMENT

In the preferred form of the invention, a relatively small amount of ethylene and vinyl acetate copolymer is added to plain paraffin or a paraffin wax composition to enhance the properties of the composition as a histological specimen embedding material. This copolymer may be in the form of pellets or dry particles which may be mixed and dissolved into the molten paraffin or both paraffin and pellets or particles may be mixed and then melted together. The addition of an effective amount of the copolymer of ethylene-vinyl acetate to a paraffin, and even to paraffins normally considered to be too soft to be useable as specimen embedding media, produces embedding compositions having good histological specimen preparation characteristics. Good cutting characteristics for producing highly satisfactory specimen sections are obtainable. Specimen slices can be very thin, for example, some formulations which include paraffin and ethylene-vinyl acetate copolymer can be sliced into high quality sections as thin as 1 micron. By employing ethylene-vinyl acetate, the commercially available supply of paraffins that can be employed in histological embedding compositions is substantially increased. Also, in those cases requiring 1-micron thick tissue sections, this paraffin based composition can be used instead of the previously mentioned methacrylate-type material. The amount of ethylene-vinyl acetate employed should be in an amount that will effect an increase in hardness of the paraffin or paraffin composition employed, as will be further discussed.

An ethylene and vinyl acetate copolymer which provided good results is manufactured by the Du Pont Company, New York, New York and known under the trademark Elvax. This ethylene-vinyl acetate copolymer has a content by weight of 28% vinyl acetate and a number of such copolymers are known as the Elvax 200 Series.

It has been found that with some paraffin waxes, the addition of a compatibilizer to the paraffin and copolymer of ethylene and vinyl acetate improves the solubility of the copolymer in the paraffin. Various compatibilizers which are surface active agents soluble in molten paraffin wax and which reduce the turbidity of the molten paraffin are beneficial in the composition containing paraffin wax and the above mentioned copolymer.

Compatibilizers have been used for some years in the polymer industry where they permit the blending of various polymers which otherwise would not remain mixed together but would eventually separate and make the molded product fail in service.

A preferred compatibilizer beneficial for the above mentioned composition of paraffin and copolymer is alkylphenylopolyethylene glycol having a sufficiently short ethylene oxide chain (for example 1 to 3 ethylene oxide units) to be soluble in molten paraffin. One such commercially available compatibilizer is sold under the name Igepal CO-210 manufactured by GAF Company of New York, New York. Also, a paraffin-soluble alkylpoklyethylene glycol as well as sorbitan esters or other polyalcohols soluble in molten paraffin wax are also beneficial as compatibilizers. Because of improved solubility, there is an increase in clearness or reduction in turbidity of the above composition when molten. This permits somewhat better viewing of the specimen during infiltration of the embedding medium into the specimen so as to ensure better against any foreign matter inadvertently coming in contact with the specimen during this step in the processing.

It is believed that the compatibilizer functions by promoting adhesion between the above copolymer and paraffin wax, and acts as a plasticizer. Also, because the compatibilizer has surface active properties it tends to increase the rate of penetration of the embedding composition. The plasticizing action is also believed to reduce thermal shock or cracking due to temperature change, reduce breakage due to mechanical shock, reduce stiffness allowing easier flattening of the slice and effect better adhesion between slices when a ribbon of slices is produced.

A preferred range of ethylene-vinyl acetate copolymer is from about 0.5% to 5%, by weight, of the paraffin. The amount of ethylene-vinyl acetate copolymer to be added to paraffin to produce good sectioning will vary somewhat with the different available paraffins, and the desired amount could vary from the above range. In the majority of the paraffin compositions prepared, the effective amount of ethylene-vinyl acetate copolymer producing good results was in the range of 0.5% to 2% by weight of the paraffin.

In those cases where a compatibilizer was used, the compatibilizer alkylphenylpolyethylene glycol or other was added to the combination of paraffin and ethylene-vinyl acetate copolymer in an amount within a preferred range from about 0.4% to about 2% of paraffin, with good results.

The tissue-embedding material may be made by thoroughly mixing and disolving the ethylene-vinyl acetate copolymer in the melted paraffin. Where used, the compatibilizer may also be thoroughly mixed and dissolved with the paraffin and ethylene-vinyl acetate copolymer while the paraffin is in the molten state. The resulting embedding composition is cooled to the hardened state and can then be used to prepare a specimen for sectioning by a microtome.

The method of specimen preparation may include dehydrating the tissue speciments, for example in alcohol, clearing the specimen such as in chloroform or xylene, melting the above embedding composition, and inserting the specimen into a bath of the molten composition so that the specimen is infiltrated or impregnated by the embedding material. Infiltration may be carried out at pressures below atmospheric pressure in order to insure against air being trapped within the specimen. After infiltration, the specimen is placed in a mold containing an additional amount of the same amount mentioned embedding composition in molten form. The embedding composition is cooled to solidify it with the specimen embedded in it. The mold may be removed or partially removed and the resulting block of solid embedding material moved to a microtome. The microtome can be operated to slice a plurality of thin sections, generally 2 to 5 microns in thickness, to form a ribbon of slices or specimen sections adhesively connected together by the medium. Sections may be separated and then deparaffinized, dehydrated, cleared and mounted on a slide for histological studies.

The following examples of tissue embedding compositions are presented by way of illustration of the invention and are not intended to limit the invention.

COMPOSITION A 241.15 grams of paraffin, identified by the trademark Mobilwax 130 and made by Mobil Oil of New York, New York, was melted. 3.041 grams of ethylene and vinyl acetate copolymer pellets were added to the molten paraffin and thoroughly mixed. The copolymer was Du Pont Elvax 240. The resulting composition was allowed to cool and solidify.

COMPOSITION B 253.745 grams of paraffin manufactured by the Conoco Company (DuPont) of Wilmington, Del., and identified as Code 720 was melted; and 3.566 grams of Elvax 240 and 4.205 grams of the compatibilizer Igepal Co-210 were dissolved in the molted paraffin and thoroughly mixed.

COMPOSTION C 250.67 grams of Mobilwax 130 paraffin were melted and 3.524 grams of Elvax 240 and 1.067 grams of GAF Igepal CO-210 dissolved and mixed in the molten paraffin.

COMPOSITION D 252.16 grams of paraffin manufactured by the Union Oil Company of San Francisco, Cal., and identified as Aristowax 125 (1981 Formulation) were melted. 3.554 grams of Elvax 220 and 2.041 grams of Igepal CO-210 were mixed and dissolved in the molten paraffin, and the composition allowed to cool and solidify.

COMPOSITION E 223.26 grams of the above Aristowax 125 were melted. 3.117 grams of Elvax 240 and 3.408 grams of a sorbitan ester known as Span 65, a sorbitan tristearate manufactured by ICI Americas of Wilmington, Del.

The above example compositions exhibited good embedding material characteristics needed for the preparation of tissue sections for histological studies. The above compositions A, B, C, D and E were used to produce specimen sections of liver, kidney, brain, skin and vertebra. Using each of the above compositions, good sections as thin as 1 micron were obtainable with specimens of kidney, liver, brain and bone. Compositions A and B produced the best 1-micron sections of liver, kidney and brain. All the above compositions produced acceptable 2- and 5- micron sections.

The above example compositions provided substantially better specimen embedding media than plain paraffin media used in the past.

The compatibilizer may be one or a combination of surface active agents. For example, the two polyethylenes, alkylphenylpolyethylene glycol and alklpolyethylene glycol can be employed together in the same embedding medium.

The Elvax, 200 Series polymers or resins all contained 750 parts per million of butylated hydroxytoluene. The Elvax 220 had a softening point of 88° C. while the Elvax 240 had a softening point 110° C.

As various changes could be made in the above description without departing from the scope of the invention, it is intended that all matter contained in the above description shall be interpreted as illustrative and not in a limiting sense.

I claim:

1. A method of preparing a histological tissue specimen for sectioning on microtome for histological analysis comprising the steps of infiltrating the specimen with a melt of an embedding composition including a paraffin surface active compatibilizer selected from the group consisting of alkylphenylpolyethylene glycol, alklpolyethylene glocol, a sorbitan ester or molten paraffin-soluable fatty acid ester of an alcohol or polyalcohol, and a copolymer of ethylene and vinyl acetate, the amount of said copolymer being sufficient to increase the hardness of the composition, said compatibilizer being soluble in molten paraffin in an amount effective to reduce turbidity of the composition when in the molten state.

2. The method of claim 1 further including the steps of placing the infiltrated specimen in a mass of molten embedding composition, solidifying the mass of embedding composition, and slicing sections of said solidified mass of embedding composition and said specimen in a microtome to produce thin slices of said mass and specimen for histological analysis.

3. The method of claim 2 wherein said mass of embedding composition is the same composition as that of said melt.

4. The method of claim 1 wherein the compatiilizer comprises an amount between about 0.4% and 2.0% by weight of the paraffin.

5. The method of claim 1 wherein about 28.0% by weight of said copolymer is said vinyl acetate.

* * * * *